United States Patent [19]

Fuchs et al.

[11] Patent Number: 4,544,508

[45] Date of Patent: Oct. 1, 1985

[54] PROCESS FOR THE PREPARATION OF CERTAIN ENANTIOMERIC PAIRS OF α-CYANO-3-PHENOXY-4-FLUORO-BENZYL PERMETHRATE

[75] Inventors: Rainer Fuchs, Wuppertal; Klaus Naumann, Leverkusen, both of Fed. Rep. of Germany

[73] Assignee: Bayer Aktiengesellschaft, Leverkusen, Fed. Rep. of Germany

[21] Appl. No.: 689,759

[22] Filed: Jan. 9, 1985

[30] Foreign Application Priority Data

Jan. 18, 1984 [DE] Fed. Rep. of Germany ....... 3401483

[51] Int. Cl.$^4$ ............................................ C07C 121/75
[52] U.S. Cl. .................................................. 260/465 D
[58] Field of Search ...................................... 260/465 D

[56] References Cited

U.S. PATENT DOCUMENTS

| | | | |
|---|---|---|---|
| 4,133,826 | 1/1979 | Warnant et al. | 260/465 D |
| 4,136,195 | 1/1979 | Warnant et al. | 424/304 |
| 4,151,195 | 4/1979 | Warnant et al. | 260/465 D |
| 4,218,469 | 8/1980 | Fuchs et al. | 424/304 |
| 4,308,279 | 12/1981 | Smeltz | 424/304 |

*Primary Examiner*—Dolph H. Torrence
*Attorney, Agent, or Firm*—Sprung, Horn, Kramer & Woods

[57] ABSTRACT

A process for the preparation of the enantiomeric pairs (1R-3R-αS+1S-3S-αR) and (1R-3S-αS+1S-3R-αR) from a mixture of all 8 stereoisomers of the compound αR/S-cyano-3-phenoxy-4-fluorobenzyl 3R/S-(2,2-dichlorovinyl)-2,2-dimethyl-1R/S-cyclopropanecarboxylate, comprising dissolving the mixture in a secondary or tertiary alkylamine having 2–6 C atoms per alkyl radical, subjecting the solution to crystallization whereby the enantiomeric pairs (1R-3R-αS+1S-3S-αR) and (1R-3S-αS+1S-3R-αR) crystallize out from the solution, and separating the crystallized material. The crystals are enriched in the most active components.

3 Claims, No Drawings

PROCESS FOR THE PREPARATION OF CERTAIN ENANTIOMERIC PAIRS OF α-CYANO-3-PHENOXY-4-FLUORO-BENZYL PERMETHRATE

The present invention relates to a process for the preparation of certain enantiomeric pairs of α-cyano-3-phenoxy-4-fluoro-benzyl permethrate starting from a mixture of all steric and optical isomers.

It is known that enantiomers of compounds possessing an acidic hydrogen atom on an asymmetric C atom can be epimerized by treatment with bases. The carbon-ions formed in the reaction with bases are converted rapidly and continuously to their possible enantiomeric forms. In this process, they pass briefly through the flat state (P. Sykes: Reaktionsaufklärung—Methoden and Kriterien der organischen Reaktionsmechanistik [Explanation of reactions—Methods and criteria of organic reaction mechanisms]; Verlag Chemie 1973, page 133, and D. J. Cram: Fundamentals in Carbanion Chemistry, page 85–105, Academic Press New 1965).

This case is also observed in, for example, the readily base-catalyzed epimerization of optically active mandelic acid nitrile of the formula

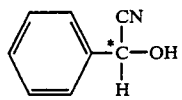

and of the corresponding methyl ether of the formula

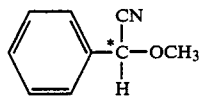

to the racemic compounds. (Smith: J. Chem. Soc. 1935, page 194 and Smith: Ber. 64 (1931), page 427.)

Depending on the solubility of the equilibrium partner of an epimerization equilibrium in the labile diastereomer, the equilibrium can be shifted to a very great extent or completely to one side if one portion crystallizes out. This case is known as "second order asymmetric transformation". (K. Mislow, Introduction to Stereochemistry, W. C. Benjamin Inc. New York, Amsterdam 1966, top of page 122).

However, this effect can only be utilized in practice when a solvent can be found in which one stereoisomer and/or its mirror image is more readily soluble, and the other stereoisomer and/or its mirror image is more poorly soluble.

Such a reaction has, for example, already been disclosed for the optically active α-cyano-(αRS)-3-phenoxybenzyl 2,2-dimethyl-3R-(2,2-dichlorovinyl)-cyclopropane-1R-carboxylate (DE-OS (German Published Specification) No. 2,718,039). Ammonia and amines are employed as bases for optimization. Acetonitrile and lower alkanols are employed as solvents. In this procedure, however, the ester of a particular enantiomer of the carboxylic acid (1R3R) is used as the starting material.

There is no indication that this method can also be employed for isolating certain stereoisomers from the racemic mixture of all 8 stereoisomers of the above compound, by epimerization of the others.

Furthermore, DE-OS (German Published Specification) No. 2,903,057 discloses that it is also possible to epimerize the 4 stereoisomeric α-cyano-(αR,S)-3-phenoxybenzyl esters of a racemic carboxylic acid at the α-carbon atom adjacent to the cyano group by treatment with bases, and to crystallize out a single enantiomeric pair from suitable solvents. In this case, too, lower alcohols, in particular methanol, are stated as being suitable solvents. Aqueous ammonia is used as the base.

According to EP-OS (European Published Specification) No. 22,382, a process for converting the stereoisomer mixture of the 4 cis isomers of α-cyano-3-phenoxybenzyl permethrate to a pure enantiomeric pair is carried out in a similar manner, by crystallizing out the more poorly soluble enantiomeric pair in a suitable solvent, by subsequent epimerization, with a base, of the other enantiomeric pair remaining in solution, and once again crystallizing out the more poorly soluble enantiomeric pair. Crystallization and epimerization are carried out in separate stages. Hydrocarbons, in particular hexane, are disclosed as suitable solvents for this procedure. Amines, in particular triethylamine, are employed as bases.

DE-OS (German Published Specification) No. 115,881 discloses another process for converting the stereoisomer mixture of all 4 cis-isomers of α-cyano-3-phenoxybenzyl 3-(2,2-dichlorovinyl)-2,2-dimethylcyclopropanecarboxylate to a single enantiomeric pair. In this process, an organic amine is used as both solvent and base. Triethylamine and diisopropylamine are stated to be very suitable for this process. Tri-n-propylamine and n-butylmethylamine are mentioned as being unsuitable. However, in this process too, a sterically pure racemic acid moiety (cis isomer) is employed. In this case, too, there is no indication as to whether individual stereoisomers can also be isolated from the mixture of all 8 possible stereoisomers.

It is not possible to predict which solvents will be suitable for the separation of enantiomers or diastereomers of the enantiomeric pairs. It is therefore necessary to develop a suitable separation system for each individual compound. Experience from cases which are similar in principle can only sometimes be extrapolated, but not in a predicable manner.

α-Cyano-3'-phenoxy-4'-fluorobenzyl 2,2-dimethyl-3-(2,2-dichlorovinyl)-cyclopropane-carboxylate (permethrate) has the structural formula I

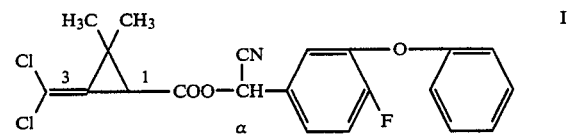

The compound possesses three asymmetric centers 1, 3 and α. It therefore exists as the following enantiomeric pairs:

| | | | |
|---|---|---|---|
| a: | 1R—3R—αR | + 1S—3S—αS | |
| b: | 1R—3R—αS | + 1S—3S—αR | 1,3 cis |
| c: | 1R—3S—αR | + 1S—3R—αS | |
| d: | 1R—3S—αS | + 1S—3R—αR | 1,3 trans |

The enantiomeric pairs b and d are particularly active against a large number of industrially important pests.

In the industrial production of the compound of the formula I, the ratios of the enantiomeric pairs a–d can be varied only within a certain narrow range. In a typical industrially produced compound of the formula I, the enantiomeric pairs a–d are present in, for example, the following ratio (relative to 100%)

a=24.5%
b=17.5%
c=34.5%
d=23.5%

It is an object of the invention to find a process in which the ratio of the enantiomeric pairs a–d in the mixture of all enantiomers is altered in favor of the enantiomeric pairs b and d.

It has been found that the enantiomeric pairs (b) 1R-3R-αS+1S-3S-αR and (d) 1R-3S-αS+1S-3R-αR can be isolated from a mixture of all 8 stereoisomers of the compound α-cyano-3-phenoxy-4-fluorobenzyl permethrate by a method in which this mixture of all stereoisomers is dissolved in a secondary or tertiary alkylamine having 2–6 C atoms per alkyl part in each case, and the mixture of the enantiomeric pairs b and d is crystallized out from the solution obtained.

It is surprising that epimerization at the C atom and isolation of the desired enantiomeric pairs can be achieved with the same solvent. It is furthermore surprising that, in order to carry out this process, it is not necessary to start from an ester possessing a sterically pure acid moiety, but that the industrially produced mixture consisting of all 8 stereoisomers of the cis and trans series can be converted to a mixture consisting essentially of 4 cis and trans stereoisomers. However, this process is also suitable for converting the 4 stereoisomers of the cis series or of the trans series alone, and for any desired mixture of cis and trans.

The process according to the invention is carried out in secondary or tertiary alkylamines, each having 2–6 C atoms per alkyl part, and mixtures of these. Amines having 4 C atoms per alkyl part may be preferably mentioned. Di-iso-butylamine, tri-iso-butylamine, tri-n-butylamine and mixtures of these may be particularly mentioned.

The amines are employed in an essentially anhydrous form. Industrial cis/trans starting material is dissolved in the amine base at 40°–80° C., preferably between 50° and 70° C. The solution is then cooled to −25 to +30° C. Crystallization can be accelerated by the addition of a few small crystals of the enantiomeric pairs b+d. However, crystallization also takes place spontaneously. The enantiomeric pairs b+d are isolated in a customary manner, for example by filtration or centrifuging.

The examples which follow illustrate the invention without restricting its scope.

For Examples 1 to 2, and industrial product having the following composition was used:

Ia=24.5%
Ib=17.5%
Ic=34.5%
Id=23.5%

EXAMPLE 1

10 g of the industrial cis/trans mixture of all 8 isomers of α-cyano-3-phenoxy-4-fluorobenzyl 3-(2,2-dichlorovinyl)-2,2-dimethyl-cyclopropanecarboxylate were dissolved, while heating to 50°–70° C., in the amount of the organic amine listed in the table. The stirred solution was allowed to cool to room temperature and was then stirred at 20° C. for the time indicated in Table 1. Crystallization generally began spontaneously after about 2–3 hours. Only when this was not the case were seed crystals of the enantiomeric pairs b and d (see above) added.

The crystals formed were then filtered off under suction and rinsed with a small amount of cold n-hexane. The dried crystals were weighted, and the isomer composition was determined by HPLC (high pressure liquid chromatography). The results are summarized in the table below.

TABLE

| Amine | Amount of amine ml | Stirring time in hours | Yield of crystalline product in g | Isomer composition in % | | | |
|---|---|---|---|---|---|---|---|
| | | | | Ia | Ib | Ic | Id |
| CH$_3$\\ /H /CH$_3$<br>   CH—CH$_2$—N—CH$_2$—CH<br>CH$_3$/ \\CH$_3$<br>di-iso-butylamine | 5 | 48 | 6.4 | 1.8 | 20.5 | 2.9 | 76.0 |
| | 10 | 48 | 5.2 | 1.5 | 13.3 | 1.8 | 83.3 |
| | 15 | 48 | 4.7 | 0.9 | 12.8 | 1.1 | 85 |
| (n-C$_4$H$_9$)$_3$N<br>tri-n-butylamine | 5 | 48 | 2.0 | — | 22.8 | 4.2 | 73 |
| | 10 | 48 | 3.0 | | | | |
| | 40 | 48 | 4.4 | | | | |
| N(C$_2$H$_5$)$_3$<br>triethylamine | 5 | 48 | 4.3 | 2.5 | 18.9 | 4.1 | 73.6 |
| | 10 | 48 | 4.1 | 2.1 | 18.2 | 2.8 | 76.9 |
| | 15 | 48 | 4.0 | 1.9 | 16.5 | 2.8 | 78.8 |

EXAMPLE 2

100 g of an industrial cis/trans mixture of all 8 stereoisomers of α-cyano-3-phenoxy-4-fluorobenzyl 3-(2,2-dichlorovinyl)-2,2-dimethyl-cyclopropanecarboxylate were dissolved in 35 ml of di-iso-butylamine, while heating to 60° C. The stirred solution was allowed to cool slowly to room temperature (20° C.). During this procedure, spontaneous crystallization began. Stirring was then continued for 48 hours at 20° C. The crystalline precipitate formed was filtered off under suction and rinsed with 25 ml of n-hexane which had been cooled to 0° C., and was sucked dry and then dried in the air until the weight remained constant. 57 g of a colorless crystalline product having a melting point of 88°–96° C. were obtained, the product having the following isomer composition determined by HPLC (relative to 100%):

a=1.8%,
b=19.7%,
c=2.8%, d=76.9%.

The filtrate was freed from amine and n-hexane in vacuo, and the remaining oil was dissolved in 200 ml of toluene. This solution was stirred with 15 g of silica gel for 5 minutes at room temperature. It was then filtered under suction, and the toluene was distilled off from the filtrate in vacuo. The remaining oil (35 g) was dissolved in a mixture of 14 g of di-iso-butylamine and 56 g of tri-n-butylamine at 60° C. After cooling to 20° C. and stirring for 48 hours, working-up was carried out as described above.

11 g of colorless crystals having a melting point of 69°–72° C. were obtained, the isomer composition (HPLC method) of the crystals being as follows:

a=1.4%,
b=77.2%,
c=0.9%,
d=19.4%.

The filtrate from the second stage was once again treated in the same way as the filtrate from the first stage. In this manner, a further 8 g of colorless crystals having a melting point of 71°–72° C. and consisting predominantly of the b isomer were obtained.

a=1.2%,
b=79.1%,
c=0.8%,
d=18.9%.

A total of 76 g of a mixture of the b and d isomers were obtained in this manner from the 3 stages.

It is understood that the specification and examples are illustrative but not limitative of the present invention and that other embodiments within the spirit and scope of the invention will suggest themselves to those skilled in the art

We claim:

1. A process for the preparation of the enantiomeric pairs (1R-3R-$\alpha$S+1S-3S-$\alpha$R) and (1R-3S-$\alpha$S+1S-3R-$\alpha$R) from a mixture of all 8 stereoisomers of the compound $\alpha$R/S-cyano-3-phenoxy-4-fluorobenzyl 3R/S-(2,2-dichlorovinyl)-2,2-dimethyl-1R/S-cyclopropanecarboxylate, comprising dissolving the mixture in a secondary or tertiary alkylamine having 2–6 C atoms per alkyl radical, subjecting the solution to crystalliztion whereby the enantiomeric pairs (1R-3R-$\alpha$S+1S-3S-$\alpha$R) and (1R-3S-$\alpha$S+1S-3R-$\alpha$R) crystallize out from the solution, and separating the crystallized material.

2. A process according to claim 1, wherein the alkyl radicals have 3–5 C atoms.

3. A process according to claim 1, wherein the amine is at least one of di-iso-butylamine and tri-n-butylamine.

* * * * *

UNITED STATES PATENT AND TRADEMARK OFFICE
CERTIFICATE OF CORRECTION

PATENT NO. : 4,544,508
DATED : October 1, 1985
INVENTOR(S) : Rainer Fuchs, et al.

It is certified that error appears in the above-identified patent and that said Letters Patent is hereby corrected as shown below:

Col. 1, line 17          Delete "and" and substitute --und--

Col. 2, line 27          Insert --3-- before "115,"

Col. 6, line 23          Delete "5" and insert --4--

Signed and Sealed this

Eighteenth Day of February 1986

[SEAL]

Attest:

DONALD J. QUIGG

Attesting Officer          Commissioner of Patents and Trademarks